(12) United States Patent
Head et al.

(10) Patent No.: US 7,290,438 B2
(45) Date of Patent: Nov. 6, 2007

(54) AUTOMATED APPARATUS AND METHOD FOR TESTING CORK WINE BOTTLE STOPPERS FOR THE PRESENCE OF AN ANALYTE THAT CAUSES CORK TAINT IN BOTTLED WINE

(75) Inventors: Michael S. Head, 15 Hibben Rd., Princeton, NJ (US) 08540; John Cronin, Essex Junction, VT (US); Mark Burrows, Newtown, PA (US); Cynthia Timblin, Burlington, VT (US)

(73) Assignee: Michael S. Head, Princeton, NJ (US)

( * ) Notice: Subject to any disclaimer, the term of this patent is extended or adjusted under 35 U.S.C. 154(b) by 0 days.

(21) Appl. No.: 11/372,848

(22) Filed: Mar. 10, 2006

(65) Prior Publication Data

US 2006/0144125 A1 Jul. 6, 2006

Related U.S. Application Data

(63) Continuation of application No. 10/701,715, filed on Nov. 5, 2003, now Pat. No. 7,010,956.

(51) Int. Cl.
*G01N 33/497* (2006.01)
(52) U.S. Cl. .................................. 73/23.34
(58) Field of Classification Search ............... 73/23.34, 73/23.2, 863.71
See application file for complete search history.

(56) References Cited

U.S. PATENT DOCUMENTS

| | | | | |
|---|---|---|---|---|
| 3,824,845 A | * | 7/1974 | Huebner | 73/769 |
| 3,902,851 A | * | 9/1975 | Dravnieks | 73/23.34 |
| 5,571,401 A | * | 11/1996 | Lewis et al. | 205/787 |
| 5,675,070 A | * | 10/1997 | Gelperin | 73/23.34 |
| 6,085,576 A | * | 7/2000 | Sunshine et al. | 73/29.01 |
| 6,295,860 B1 | * | 10/2001 | Sakairi et al. | 73/23.41 |
| 6,354,160 B1 | * | 3/2002 | Staples et al. | 73/863.12 |
| 6,435,002 B1 | * | 8/2002 | Briggs | 73/23.2 |
| 6,450,008 B1 | * | 9/2002 | Sunshine et al. | 73/23.34 |
| 6,541,260 B1 | * | 4/2003 | Pariseau et al. | 436/24 |
| 6,572,818 B1 | * | 6/2003 | Clauzure et al. | 422/26 |
| 6,695,997 B2 | * | 2/2004 | Yaniger | 264/45.9 |
| 6,733,706 B2 | * | 5/2004 | Allman et al. | 264/50 |
| 6,772,892 B2 | * | 8/2004 | Flesher | 215/249 |
| 7,010,956 B2 | * | 3/2006 | Head et al. | 73/23.34 |

FOREIGN PATENT DOCUMENTS

WO    WO 3041927 A1 * 5/2003

* cited by examiner

*Primary Examiner*—Hezron Williams
*Assistant Examiner*—John Fitzgerald
(74) *Attorney, Agent, or Firm*—Downs Rachlin Martin PLLC

(57) ABSTRACT

An apparatus and method for automatedly detecting the presence of one or more chemical contaminants, such as 2,4,6-trichloroanisole, in/on a plurality of cork wine bottle stoppers in rapid succession using electronic nose chips. The apparatus moves the nose chips and the cork stoppers independently to align the cork stopper and a corresponding electronic nose chip with one another for testing. The automated apparatus and method provides a low-cost, reliable process for testing 100% of cork wine bottle stoppers in a fast and cost-effective manner.

13 Claims, 5 Drawing Sheets

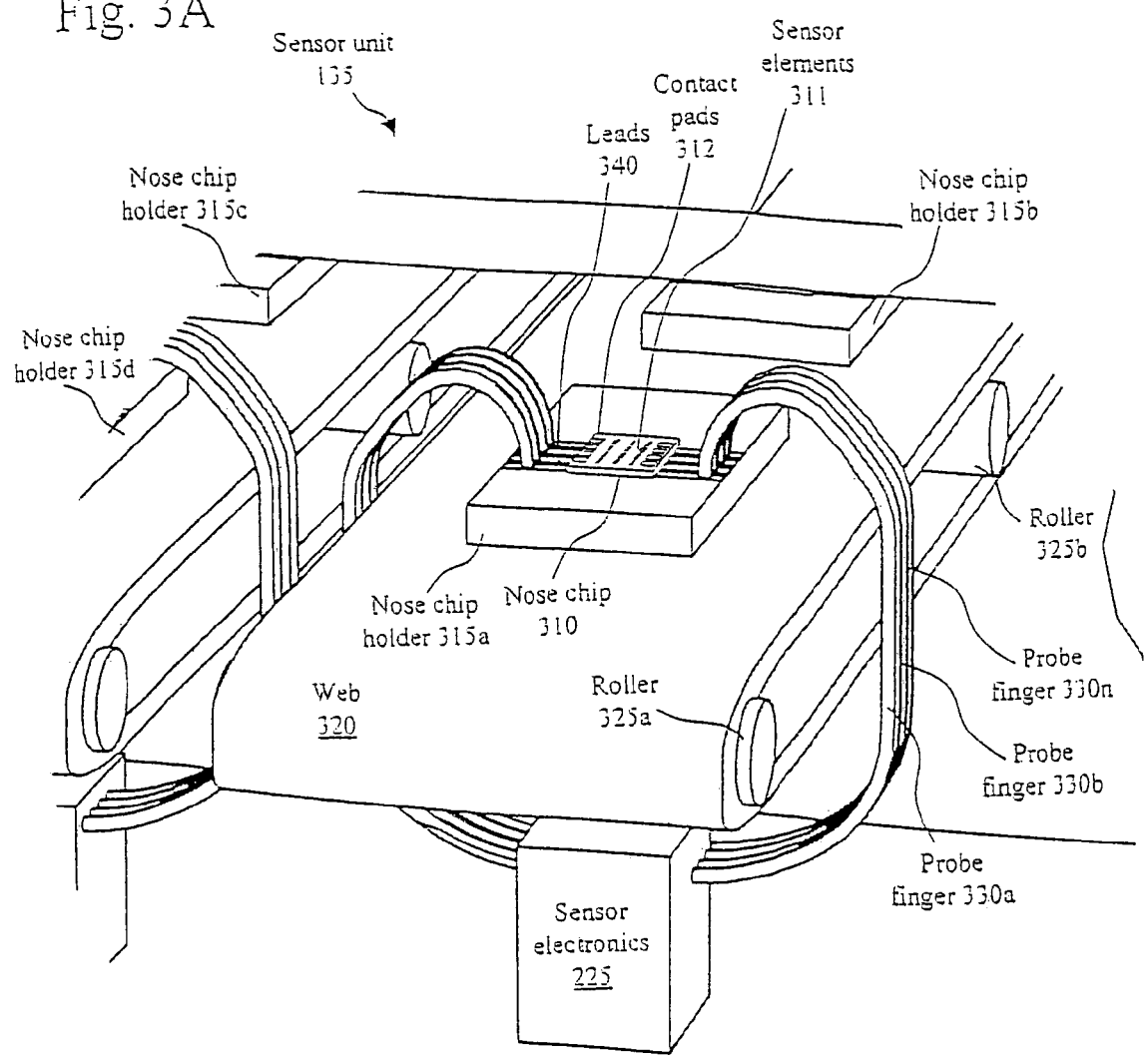

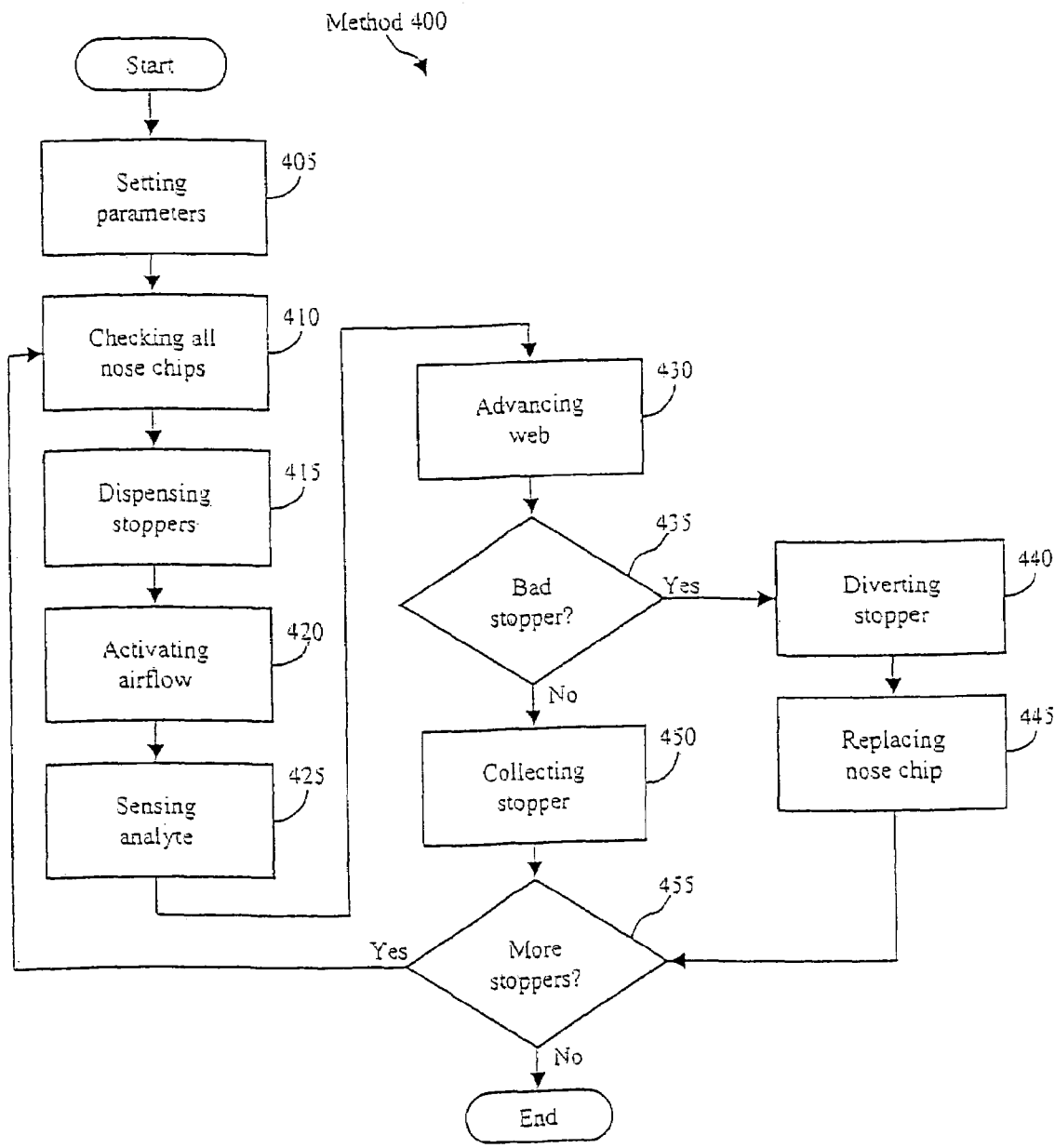

AUTOMATED APPARATUS AND METHOD FOR TESTING CORK WINE BOTTLE STOPPERS FOR THE PRESENCE OF AN ANALYTE THAT CAUSES CORK TAINT IN BOTTLED WINE

RELATED APPLICATION DATA

This application is a continuation of U.S. patent application Ser. No. 10/701,715, filed Nov. 5, 2003, and titled "APPARATUS AND METHOD FOR DETECTING AN ANALYTE," now U.S. Pat. No. 7,010,956, which is incorporated by reference herein in its entirety.

FIELD OF THE INVENTION

The present invention generally relates to the field of wine bottling and, more particularly, to an automated apparatus and method for testing cork wine bottle stoppers for the presence of an analyte that causes cork taint in bottled wine.

BACKGROUND OF THE INVENTION

The wine industry produces approximately fourteen billion bottles of wine per year. The bottled wines range in price from inexpensive table wines to very expensive, high-quality wines. The more expensive wines (i.e., from fifty dollars to thousands of dollars per bottle) are typically produced by a small number (presently, about two thousand) of high-end wineries that produce 200,000 to 80 million bottles of wine each per year.

Most bottled wines, both inexpensive and expensive, are sealed with cork stoppers. Cork stoppers include natural cork stoppers punched from strips of bark and less expensive molded or extruded agglomerated cork with natural cork discs on each end. Wine makers generally prefer cork stoppers for sealing their bottles to maintain the traditional wine-opening experience that consumers expect. Unfortunately, the use of cork stoppers can adversely affect the taste of wine, a characteristic commonly referred to as "cork taint." Cork taint describes the "off" smell and taste imparted to wine from chemical contaminants such as 2,4,6-trichloroanisole (TCA) in the cork stopper.

The incidence of cork taint is sporadic and random, typically affecting 1-2% of bottled wines. Since cork taint takes effect after bottling, it cannot be detected until after a bottle has been opened. Cork taint manifests as very undesirable aroma and flavor characters that are imparted to bottled wines following contact with the cork. There is nothing more offensive and embarrassing for wine consumers and producers alike than for their wine to be rated as "spoiled." For consumers, opening a cork-tainted bottle of wine can be socially embarrassing, particularly if it is an expensive bottle of wine. For wine collectors, the 1-2% incidence of cork taint imparts uncertainty about the entire wine collection. For producers, cork-tainted wine can damage their reputation, causing consumers to question the integrity and quality of their wine. Thus, there exists a need for a means to ensure the quality of cork stoppers used to bottle wines.

The chemical compound contributing most significantly to cork taint is TCA, which is implicated in more than 80% of cork-tainted wines. The production of TCA is the result of complex chemical mechanisms, including the conversion of chlorophenols to chloroanisole by common microorganisms, such as fungi, in the presence of moisture. Chlorophenols are typically used as pesticides and wood preservatives, and, consequently, they are common environmental pollutants. The uptake of even minute amounts of chlorophenol by the bark of a cork tree at any stage during its growth can yield corks that will produce cork taint in wine. Alternatively, cork taint can be the result of interaction between naturally occurring fungi in the tree bark and chlorine, a chemical commonly used to sanitize the cork. Cork, like any other wine input, therefore demands exhaustive quality control.

Quality assurance at every step of the cork stopper manufacturing process is a major concern of the cork industry. This concern has led to the implementation of the "International Code of Cork Stoppers Manufacturing Practices." The code establishes quality-control standards throughout the production process and aims to provide guarantees to cork suppliers, wine producers, and bottlers that they have a product that is free from contamination.

In addition, premium cork suppliers also insist on rigorous quality-control testing of their cork stoppers for TCA. Current industry practices for quality-control testing of cork stoppers include sensory-based methods (i.e., olfactory detection or human experts) and chemical analysis (e.g., cork soaks and gas chromatography/mass spectroscopy). However, these testing procedures are limited to testing batches of cork stoppers (e.g., statistical sampling). For example, for every 100 million or more cork stoppers produced, only a half-million to one million are tested for TCA. The batch sampling approach does not eliminate the possibility that a TCA-tainted cork will be undetected during quality-control testing and subsequently used by a wine producer or bottler. Thus, there exists a need for a testing process that provides 100% testing of cork stoppers for TCA prior to bottling.

Another limitation of current testing methods is that they are expensive and time consuming. Further, sensory-based methods that rely on human experts are subjective, variable and exhaustible. Thus, there exists a need for a low-cost, reliable testing process that provides 100% testing of cork stoppers for TCA prior to bottling.

The wine industry, seeking to increase consistency and consumer loyalty, has investigated alternative quality-control procedures. One alternative is the application of electronic nose technology to quality-control testing at all stages of wine production, e.g., bottling. An electronic nose is a sensing device capable of producing a fingerprint of specific odors. Current technology includes electronic noses that use odor-reactive polymer sensor arrays and a pattern-recognition system (i.e., e-Nose) and gas chromatography coupled to surface acoustic wave sensors (i.e., z-Nose). In one example of polymer sensor arrays, the electronic nose uses a one-inch-square microelectrical mechanical systems (MEMS) chip containing 32 pinhead-sized receptors forming a sensor array. The receptors are constructed from a conductive carbon black material blended with specific nonconductive polymers (manufactured by Cyrano Sciences, Inc., Pasadena, Calif.). When the MEMS chip is exposed to a specific vapor, a corresponding receptor expands, temporarily breaking some of the connections between the carbon black pathways and thereby increasing the electrical resistance in the sensor. Signals from the sensors are electronically processed by a microprocessor that interprets the data by using the pattern-recognition system to identify and/or quantify a specific odor contained in the vapor.

Application of electronic nose technology to quality-control monitoring of agricultural products is exemplified in U.S. Pat. No. 6,450,008 to Sunshine et al., entitled, "Food applications of artificial olfactometry." The Sunshine et al.

patent describes a method and device for evaluating agriculture products and, more particularly, for assessing and monitoring the quality of food products by using electronic noses. The quality control monitoring device includes two sensor arrays for comparative monitoring of an agricultural product, e.g., before and after a processing step such as blending or mixing, or detection of a contaminant (e.g., microorganism) relative to a clean sample. However, the quality-control monitoring device is a single device that typically requires up to three minutes to obtain a result and to cycle to the next measurement, thus limiting the number of measurements that can be determined by a single device. Further, the existing devices are expensive, which precludes purchasing multiple instruments to achieve 100% testing of a product in a production process. Thus, there exists a need for a means to test 100% of all corks in a fast and cost-efficient way.

The introduction of a new technology platform (e.g., electronic nose technology) into an existing industry (e.g., the wine industry) is often a difficult and expensive process. Often, a new technology platform is implemented by high-end or specialty producers (e.g., high-end wine producers), for which the costs associated with the production of a quality product are generally higher and the benefits provided by the new technology are initially greater. However, this approach neglects the general consumer market (e.g., inexpensive table wines), in which the volume of products consumed offers greater potential returns. Thus, there exists a need for a means to test 100% of all corks at production speed that is cost-efficient and scalable to the general consumer market.

SUMMARY OF THE INVENTION

In one aspect, the present invention is directed to a method of testing a plurality of cork wine bottle stoppers for the presence of an analyte known to cause cork taint in wine. The method comprises automatedly moving a first one of the plurality of cork wine bottle stoppers to a first position. A first sensor is automatedly moved to a second position proximate the first position. The first sensor is operatively configured to detect the presence of the analyte. It is determined via the first sensor whether the analyte is present in/on the first one of the plurality of cork wine bottle stoppers. The first one of the plurality of cork wine bottle stoppers is automatedly moved out of the first position. The first sensor is automatedly moved out of the second position. A second one of the plurality of cork wine bottle stoppers is automatedly moved into the first position. A second sensor is automatedly moved to the second position. The second sensor is operatively configured to detect the presence of the analyte. It is determined via the second sensor whether the analyte is present in/on the second one of the plurality of cork wine bottle stoppers.

In another aspect, the present invention is directed to a method of testing cork wine bottle stoppers for the presence of an analyte known to cause cork taint in wine. The method comprises providing at least 100 candidate cork wine bottle stoppers. The at least 100 candidate cork wine bottle stoppers are fed into an automated testing system comprising a plurality of electronic noses sensitive to the analyte. The automated testing system is caused to test each of the at least 100 candidate cork wine bottle stoppers for the presence of the analyte in rapid succession with others of the at least 100 candidate cork wine bottle stoppers using the plurality of electronic noses and to separate the at least 100 candidate cork wine bottle stoppers into an accepted set and a rejected set.

In yet another aspect, the present invention is directed to a cork sorting apparatus comprising a plurality of electronic noses each operatively configured to detect a chemical contaminant known to cause cork taint in wine. A stopper conveying system is operatively configured to hold and move each cork wine bottle stopper of a plurality of cork wine bottle stoppers in rapid succession to a first position. An electronic nose system is operatively configured to move each electronic nose of the plurality of electronic noses, in seriatim, to a second position proximate the first position in concert with the first system. Sensor electronics are operatively configured to identify from within the plurality of cork wine bottle stoppers via the plurality of electronic noses accepted cork wine bottle stoppers and rejected cork wine bottle stoppers. A sorting system is operatively configured to separate the rejected cork wine bottle stoppers from the accepted cork wine bottle stoppers.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein:

FIG. 3A is an enlarged perspective view of one of the sensor units of the testing apparatus of FIG. 1;

FIG. 4 is a flow diagram of a method of using the testing apparatus of FIG. 1 to detect the presence of an analyte in a plurality of items, wherein the items are cork stoppers.

DETAILED DESCRIPTION OF THE INVENTION

Generally, the present invention is an apparatus and method for detecting an analyte and, more particularly, assessing and monitoring items, such as cork stoppers, for the presence of one or more chemical contaminants or other analytes using electronic noses or other sensors. In one embodiment, the invention uses sensors and detection sensor electronics that are separate from one another such that inexpensive sensors may be reused or discarded with a rejected item. The testing apparatus moves the sensors and items independently to align a sensor and item with a detection sensor unit and/or move each sensor into electrical contact with the detection sensor electronics.

The testing apparatus may utilize multiple sensor units to simultaneously test multiple items (e.g., cork stoppers) for a chemical contaminant (e.g., TCA). The invention provides a low-cost, reliable testing process for testing up to 100% of the items at production speed in a cost-effective way that is scalable to the general consumer market. Although the present invention is particularly described in connection with testing bottle stoppers made of cork for the presence of a particular analyte, those skilled in the art will readily appreciate that the invention can be adapted for testing virtually any type of item made of any type of material for the presence of one or more of a wide variety of analytes susceptible to detection by various sensors.

Figure 1:
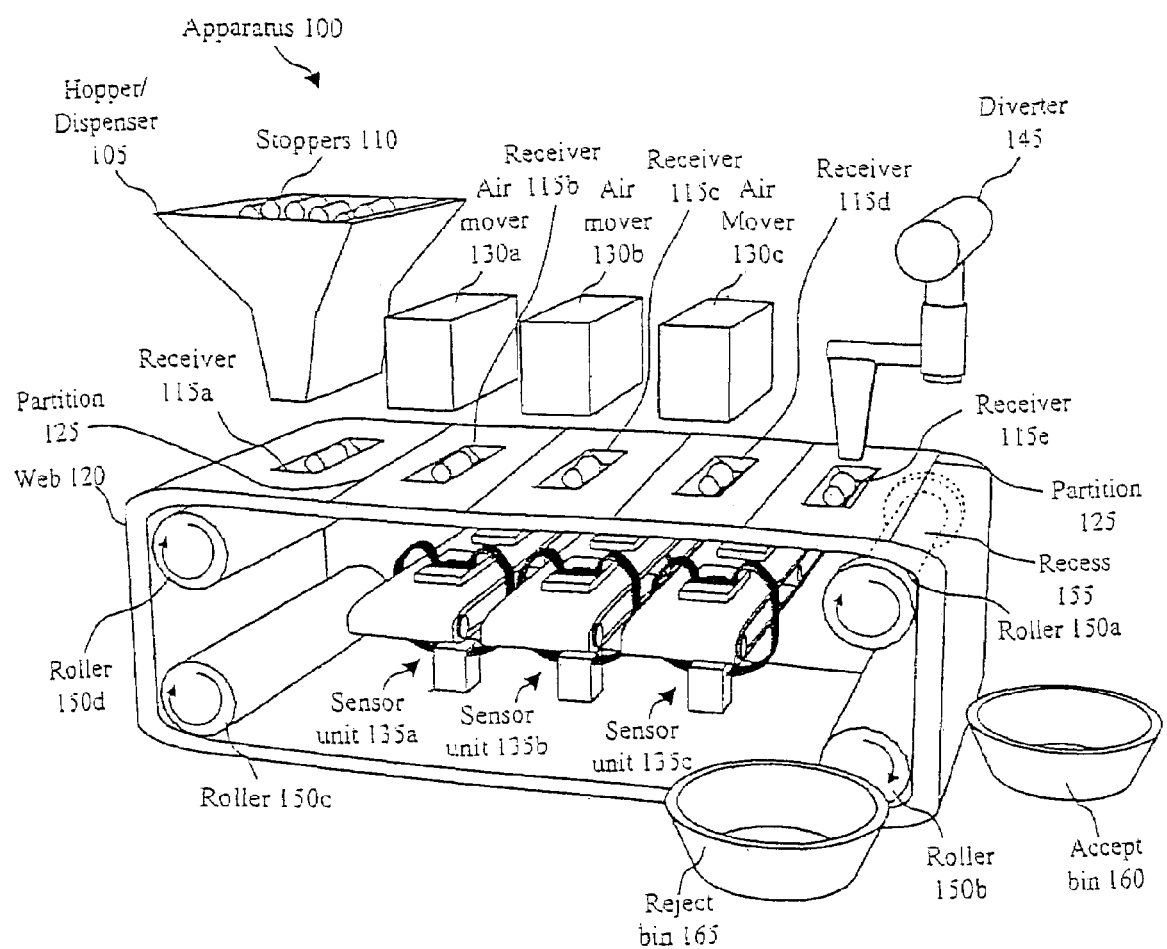
FIG. 1 is a perspective view of a testing apparatus of the present invention for detecting the presence of an analyte.

Referring now to the drawings, FIG. 1 shows in accordance with the present invention a testing apparatus, which is generally denoted by the numeral 100. As mentioned, apparatus 100 may be adapted for testing virtually any items, but in the present example items are cork stoppers 110. Apparatus 100 may include, among other things, a hopper/dispenser 105, a plurality of receivers 115 (e.g., receivers 115a, 115b, 115c, 115d and 115e), a web 120, a plurality of partitions 125, a plurality of air movers 130 (e.g., air movers 130a, 130b, and 130c), a plurality of sensor units 135 (e.g., sensor units 135a, 135b, and 135c), a diverter 145, a plurality of rollers 150 (e.g., rollers 150a, 150b, 150c, and 150d), a recess 155, an accept bin 160 and a reject bin 165.

Hopper/dispenser 105 is a storing and dispensing device for stoppers 110 to be tested. Hopper 105 may be suspended over web 120 and controlled such that a single stopper 110 is dispensed into each receiver 115. In alternative embodiments, hopper/dispenser 105 may be replaced with another device or mechanism, e.g., a conveyor or gated chute, that provides the same functionality of storing and/or delivering stoppers 110 to web 120 or other means for moving stoppers 110.

Receivers 115 may be formed in web 120 such that they are open receptacles for stoppers 110. The top opening of each such receiver 115 should be sufficiently large to receive one of stoppers 110. Depending upon the location of sensor units 135 relative to web 120, e.g., above or below, receiver 115 may include a bottom opening (not shown) that allows air to flow through the web. The bottom opening of each receiver 115 should be of sufficient size to retain stopper 110 on web 120 and provide sufficient airflow through web 120 to enable the detection of the analyte(s), if present, at sensor units 135. Each stopper 110 may be helped into its proper position within receivers 115 by corresponding partitions 125 that provide a physical barrier between adjacent receivers.

Web 120 may be a continuous belt that is positioned around rollers 150 and formed of any suitable material, such as polyurethane or rubber that provides a sturdy, flexible support for stoppers 110. Web 120 may be advanced, e.g., in a clockwise rotation, by rollers 150 or another means, not shown. Rollers 150 may be formed of any suitable material such as rubber or metal and may further include a recess 155 that facilitates passage of receivers 115 as web 120 is advanced. Of course, many alternatives to web 120 and rollers 150 exist for moving stoppers 110 into their testing positions proximate corresponding sensor units 135. Such alternatives include other types of linear conveyors and rotational moving devices, among others. In other alternative embodiments, stoppers 110 may be fed to each sensor unit 135 by a feeder system dedicated to that sensor unit.

Sensor units 135 may be located in close proximity to receivers 115, e.g., directly below the upper horizontal portion of web 120. Of course, in other embodiments of apparatus 100, sensor units 135 may be located in other suitable locations where testing can be effected, such as laterally adjacent to or above receivers 115. Details and description of sensor units 135 are discussed below in connection with FIG. 3A.

Air movers 130 may by conventional air-moving devices that provide a flow of air over stoppers 110 in receivers 115 and to sensor units 135. In the embodiment shown, air movers 130 are blowers located opposite corresponding sensor units 135 relative to corresponding receivers 115. However, air movers 130 may be suction/blower devices located between corresponding receivers 115 and sensor units 130 or opposite the receivers relative to the sensor units. The airflow provided by air movers 130 is any airflow suitable to extract chemical vapors from stoppers 110. For example, air movers 130 may be adapted to provide treated air, such as heated or pressurized air or nitrogen ($N_2$), and/or to facilitate removal of chemical vapors from stoppers 110 in receivers 115. Depending upon factors such as the volatility and dispersion properties and amount(s) of the analyte(s) at issue and the proximity and sensitivity of sensor units 135, air movers may not be required.

Diverter 145 may be provided to divert one or more contaminated stoppers 110 at a time from web 120 to prevent the rejected stoppers from being processed further along with the non-rejected, or "good," stoppers. Diverter 145 may be any suitable device, such as a movable arm, and may divert the rejected ones of stoppers 110 to any suitable container, e.g., reject bin 165, or location, e.g., a reject conveyor (not shown). Reject bin 165, if provided, may be any suitable collection container that functions to hold rejected stoppers 110 (e.g., those determined to be contaminated with TCA). Similarly, accept bin, if provided, may be any suitable collection container that functions to hold accepted stoppers 110 (e.g., those determined to be not contaminated with TCA).

Figure 2:
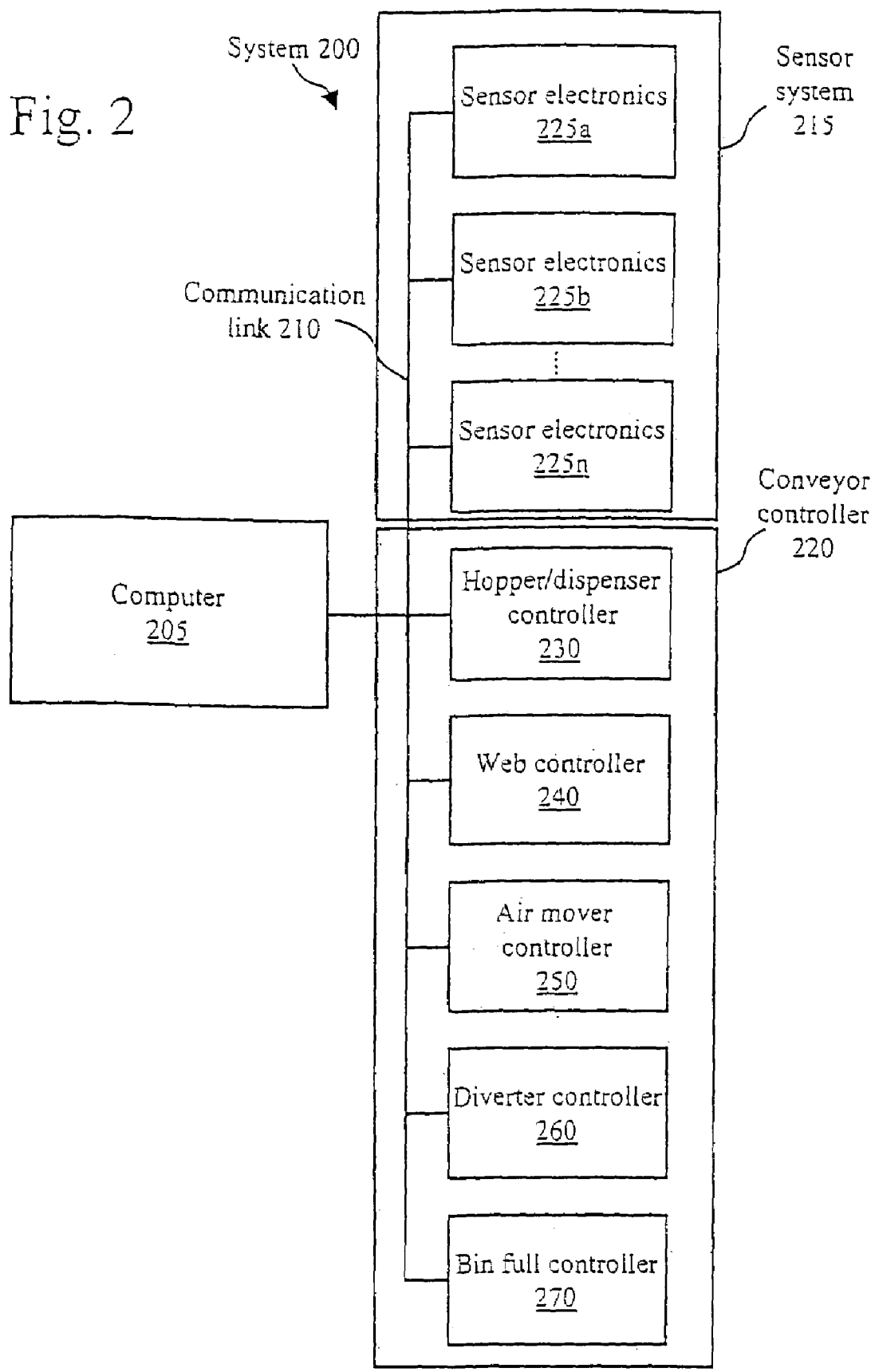
FIG. 2 is a high-level schematic diagram of a system of the present invention for operating the testing apparatus of FIG. 1.

FIG. 2 is a high-level block diagram of a control system 200 for operating apparatus 100 of FIG. 1. In one embodiment, control system 200 may include a computer 205, a communication link 210, a sensor system 215 and a conveyor controller 220. Computer 205 may be any special-purpose or general-purpose computer, such as a desktop, laptop, or host computer having a processor, memory and storage (not shown) sufficient to run software applications for operating apparatus 100.

Sensor system 215 may include a plurality of sensor electronics 225 (e.g., sensor electronics 225a, 225b and 225n, where n indicates the corresponding sensor unit 135 in apparatus 100). Sensor electronics 225 includes the electronic circuitry, such as a power regulator, processor, memory and storage, sufficient to interface sensor system 215 to computer 205 so as to operate sensor units 135 of apparatus 100. Sensor electronics 225 may further include the necessary circuitry, such as power regulator, processor, memory and storage, sufficient to run software applications (e.g., pattern signal handling capability and sensor pattern recognition algorithms) for sensor units 135 as described in more detail in reference to FIG. 3B. Such sensor electronics 225 can be readily designed by a person having ordinary skill in the art such that a detailed explanation of the sensor electronics is not necessary for those skilled in the art to understand and practice the present invention.

Conveyor controller 220 may include sub-controllers, e.g., a hopper/dispenser controller 230, a web controller 240, an air mover controller 250, a diverter controller 260 and a bin-full controller 270, to run the corresponding components of apparatus 100. Hopper/dispenser controller 230 may include software algorithms to control the mechanical operation of hopper/dispenser 105 of apparatus 100. For example, hopper/dispenser controller 230 may control the dispensing of stoppers 110 into receivers 115. Web controller 240 may include software algorithms to control the mechanical operation of web 120 of apparatus 100. For example, web controller 240 may control the rotation of rollers 150 to advance web 120.

Air mover controller 250 may include software algorithms to control the mechanical operation of air mover 130 of apparatus 100. For example, air mover controller 250 may control the flow of heated air from air movers 130 over stoppers 110 in receivers 115 and onto sensor units 135. Diverter controller 260 may include software algorithms to control the mechanical operation of diverter 145 of apparatus 100. Diverter controller 260 may be electrically connected to sensor units 135.

Bin-full controller 270 may include software algorithms to control the mechanical operations of accept bin 160 and reject bin 165 of apparatus 100. For example, bin full controller 270 may monitor the levels of stoppers 110 in accept bin 160 and reject bin 165 and indicate to computer 205 when accept bin 160 or reject bin 165 needs to be emptied.

Conveyor controller 220 and sensor system 215 may communicate with computer 205 via communication link 210, which may be any suitable wired or wireless communications link. For example, communication link 210 may be a universal serial bus (USB) and may transmit data bi-directionally between computer 205 and sensor system 215, and between computer 205 and conveyor controller 220. Alternatively, communication link 210 may be a wireless link, such as an infrared or radio frequency link, among others.

FIG. 3A shows one of sensor units 135. The others of sensor units 135 may be identical to the sensor unit shown for parallel testing of multiple stoppers 110 for the presence of the same analyte. However, the others of sensor units, if provided, may be different from the sensor unit shown. For example, one or more of the other sensor units 135 may be configured for different types of sensors for sensing other types of analytes. Each sensor unit 135 may include sensor electronics 225, a plurality of nose chips 310 (only one being shown) or other sensors, a plurality of nose chip holders 315 (e.g., holders 315a, 315b, 315c, 315d) a web 320, a plurality of rollers 325 (e.g., rollers 325a and 325b), and a plurality of probe fingers 330 (e.g., probe fingers 330a, 330b and 330n, where n corresponds to the number of probe fingers needed to make nose chips 310 test-functional). Probe fingers 330 are in electrical communication with sensor electronics 225.

Each nose chip 310 may include a plurality of sensor elements 311 and a plurality of contacts 312. Each nose chip holder 315 may include a plurality of electrical leads 340 electrically connected to corresponding ones of contacts 312 and disposed on the holder such that when that holder is in its sensing position beneath a corresponding receiver 115 (FIG. 1) containing one of stoppers 110 to be tested, the leads and probe fingers 330 may be contacted together so as to activate the corresponding nose chip 310 for testing that stopper. Such contact may be effected by moving nose chip holder 315 and/or probe fingers 330 into contact with one another.

Each nose chip 310 may include a sensor array containing a plurality of sensor elements 311 that detects a chemical analyte, such as TCA. Electrical traces or leads (not shown) may extend from sensor element 311 to contact pads 312 to electrically connect them to one another. Suitable sensor arrays include, but are not limited to, bulk conducting polymer films, semiconducting polymer sensors, surface acoustic wave devices, and conducting/nonconducting regions sensors. In one example, each nose chip 310 is a conducting/nonconducting region sensor in which conducting materials and nonconducting materials are arranged in a matrix (i.e., a resistor) and provide an electrical path between electrical leads. The nonconductive material may be a nonconducting polymer, such as polystyrene. The conductive material may be a conducting polymer, such as carbon black, an inorganic conductor. In use, the resistor provides a difference in resistance between the electrical leads when contacted with an analyte. In one example, nose chip 310 includes a sensor array specific for detection of a single analyte, such as TCA. Alternatively, nose chip 310 may include a sensor array for detecting two or more compositionally different analytes.

Each nose chip 310 may be attached to a corresponding nose chip holder 315 via wire bonds (not shown) between contact pads 312 and leads 340 on nose chip holders 315. Leads 340 may be formed of any suitable material, such as a metal foil for conducting electrical current between nose chips 310 and probe fingers 330. Probe fingers 330 provide a mechanical means to electrically connect nose chip holders 315 to sensor electronics 225. Probe fingers 330 may provide standard electrical connections for lines, such as electrical power, ground, data input, and data output. Alternatively to providing probe fingers 330, each nose chip 310 or nose chip holder 315 may have an on-board power supply (not shown), e.g., battery, for providing power to that nose chip and a wireless communication device (not shown), e.g., an infrared or radio frequency transceiver, for providing the communication link between the nose chip and sensor electronics 225.

Nose chip holders 315 may be attached to and carried by web 320, which may be formed of any suitable material, such as polyurethane or rubber, which provides a suitable support for the nose chip holders. Web 320 may be a continuous belt that is positioned around rollers 325. Web 320 may be advanced, for example, in a clockwise rotation, by rollers 325 to align nose chips 310 with sensor electronics 225. If finger probes 330 or other contact-type links are provided, they may be moved into contact with leads 340 using a suitable actuator (not shown) that may move the probes and/or sensor electronics 225. Alternatively, when one of nose chip holders 315 is in its sensing position, that holder may be moved into contact with finger probes 330, e.g., using an elevator (not shown) or other means. Rollers 325 may be conventional rollers formed of any suitable material, such as rubber or metal.

Nose chip holders 315 may be provided in any number on web 320 to suit a particular design. For example, if nose chips 310 are recycled, i.e., used over to test at least a second stopper 110 (FIG. 1), the number of chip holders 315 and nose chips 310 will generally depend upon the recycle time, i.e., the time it takes a nose chip to recover from a worst-case analyte detection so as to be ready to detect the presence of the analyte again, and the frequency of the testing. For example, if the maximum recycle time for nose chips 310 is 60 seconds and the frequency of the testing is 0.5 seconds, then the number of nose chip holders 315 and nose chips should be greater than 60/0.5=120 to allow sufficient time for the worst-case nose chip(s) to recycle for another test. Alternatively, if nose chips 310 are not recycled but rather used only once, the number of nose chip holders 315, if such holders are needed at all, may be practicably as few as two for a web-type delivery system, e.g., one of the two holders may be loaded with a fresh nose chip 310 while the other one is being used for a test. Then, the used nose chip may be removed from its holder as the fresh nose chip is moved into position for testing. Of course, more than two nose chip holders 315 may be used if desired. A single nose chip holder 315 may also be used, but would not be as efficient as having two or more such holders. Those skilled in the art will readily appreciate that nose chips 310 and/or nose chip holders 315 may be delivered to their testing locations by means other than a web-type conveyor. Such alternatives include other types of linear conveyors, rotational moving devices, ribbon-type feeding devices and cartridge-type feeding devices, among others.

Nose chip holders 315 and/or nose chips 310 may be covered with a removable cap (not shown) to protect nose chips 310 prior to a testing event. The arrangement of nose chip holders 315 and nose chips 310 on web 320 contains sufficient spacing between adjacent nose chip holders 315 such that nose chips 310 are not contaminated by overflow air during a testing event. For example, nose chip holders 315b, 315c and 315d are sufficiently spaced from nose chip 310 such that when air is passed over nose chip 310, the nose chips on nose chip holders 315b, 315c, and 315d are not contaminated by overflow air when nose chip 310 is used to test stopper 110 (FIG. 1).

Figure 3B:
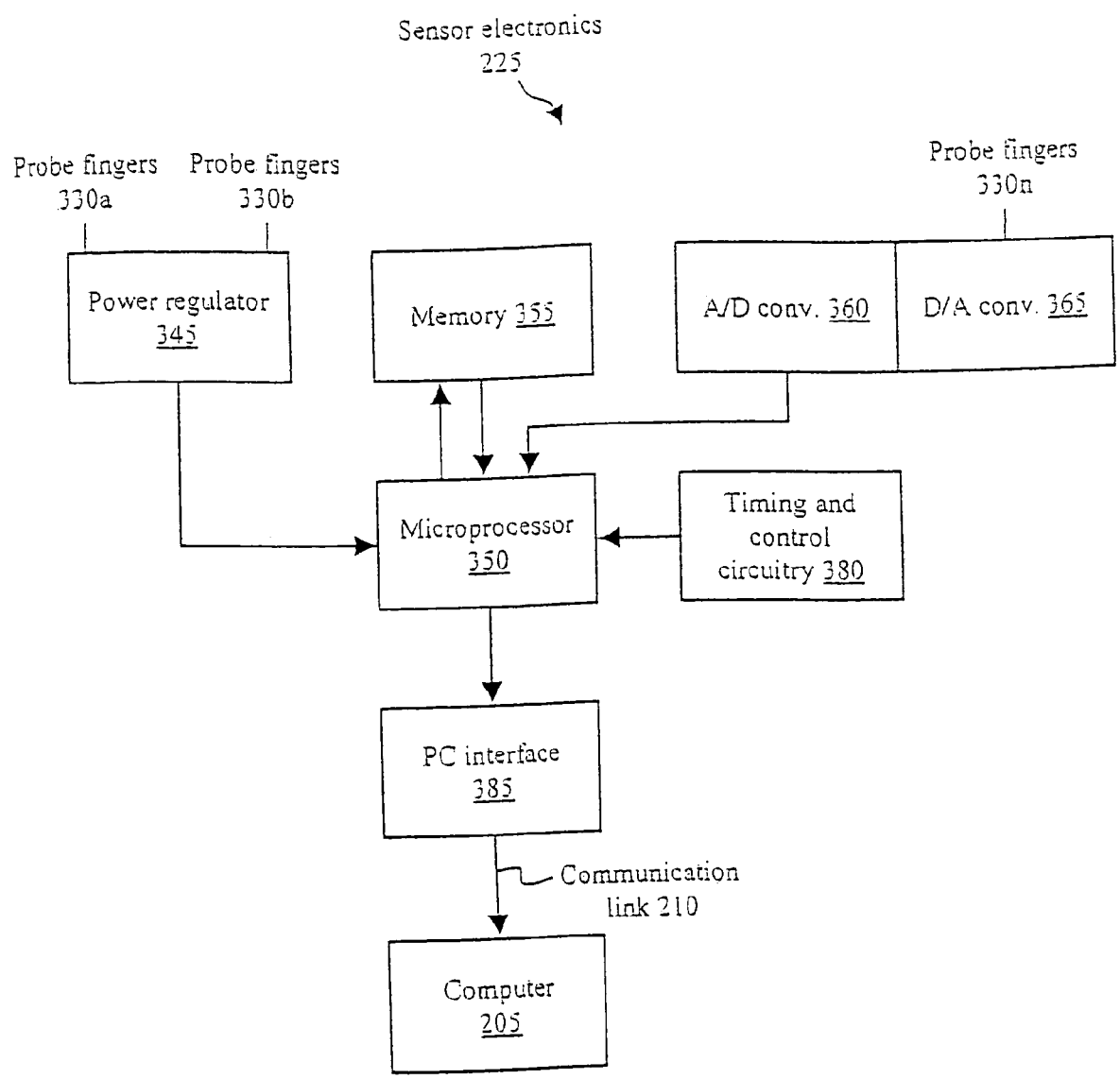
FIG. 3B is a high-level schematic diagram of the sensor electronics of the testing apparatus of FIG. 1.

Referring to FIG. 3B, sensor electronics 225 may include a power regulator 345, a microprocessor 350, a memory 355, an analog-to-digital (AID) converter 360, a digital-to-analog (D/A) converter 365, a timing and control circuitry 380 and a computer interface 385. Power regulator 345 may provide electrical power to microprocessor 350, nose chip holders 315 and nose chips 310. As mentioned above, electrical power to nose chip holders 315 and nose chips 310 may be provided via probe fingers 330. For example, electrical power may be provided by probe finger 330a and ground provided by probe finger 330b. Power regulator 345 may provide a regulated or limited amount of power to nose chip holders 315 and nose chips 310 to optimize performance of nose chips 310.

Microprocessor 350 may include the necessary processing electronics to extract and execute instructions stored in memory 355. Such processing electronics are well-known in the art and, therefore, need not be described in detail herein for those skilled in the art to understand and practice the present invention. Memory 355 may provide storage of program codes, data, and other information. Examples of program code stored in memory 355 include program code that coordinates the operation of sensor units 135 and sensor pattern signal handling and pattern recognition algorithms or look-up tables to analyze data from nose chips 310.

A/D converter 360 may provide analog-to-digital conversion of data (e.g., resistance measurements) as it passes from nose chips 310 to microprocessor 350 for further processing. D/A converter 365 may provide digital-to-analog conversion of data as it passes from microprocessor 350 to nose chips 310. Timing and control circuitry 380 may provide, for example, timing signals for data acquisition from nose chips 310 and indexer functions to coordinate the advancement of web 320 by rollers 325. Interface 385 facilitates communication between sensor electronics 225 and computer 205 and is in communication with computer 205 via communication link 210.

The identification of an analyte may occur as follows. Power regulator 345 provides an electrical signal to nose chips 310. A series of electrical traces (not shown) from each one of sensor elements 311 of nose chips 310 are connected to provide an electrical path through leads 340 and probe fingers 330 to A/D 360 and microprocessor 350. Microprocessor 350, using instructions stored in memory 355 and in timing and control circuitry 380, converts an electrical signal generated from sensor elements 311 of nose chips 310 into a processed output signal. The instructions stored in memory 355 may include, e.g., a look-up table that compares incoming signals to stored reference values to provide an analysis. Alternately, an algorithm or other analytical means for providing a chemical analysis can be provided. In the presence of an analyte, e.g., TCA, a change in electrical resistance is detected and processed by microprocessor 350. The results are output via interface 385 and communication link 210 to computer 205.

FIG. 4 illustrates a method 400 of using apparatus 100 of FIG. 1 to provide screening of 100% of cork stoppers produced by a cork stopper manufacturer. Of course, method 400 and apparatus 100 may be adapted for testing of virtually any item other than a cork stopper, e.g., packaging, such as containers, lids, caps, etc., for foods and beverages. FIGS. 1-3 are referenced throughout the steps of method 400, which may include the following steps. Those skilled in the art will recognize that method 400 is merely exemplary. Accordingly, the various steps of method 400 may be modified, deleted or replaced as needed to suit a particular design.

Step 405: Setting Parameters

In this step, a user sets parameters for the testing operations desired. Examples of testing parameters include the number of stoppers 110 to be tested, the analyte(s) to be detected (e.g., TCA), acceptable concentration levels, i.e., testing thresholds, for the analyte(s), and baseline resistance values for sensor elements 311 for re-use calibration. Testing thresholds may be adjustable/selectable, e.g., to allow for quality variations or suit the particular items being tested. Testing threshold ranges will typically be dependent upon the sensitivity of nose chips 310 or other sensor to the analyte(s) being tested. For example and with regard to TCA, the most adept humans have a detection threshold of about 10-20 parts-per-trillion (PPT) in air. Consequently, it is desirable that nose chips 310 be able to detect the presence of TCA at a level lower than 10-20 PPT at the same conditions. Method 400 proceeds to step 410.

Step 410: Checking all Nose Chips

In this step, sensor unit 135 performs a scan of nose chips 310 on web 320 to ensure that all nose chips 310 are operational. For example, sensor electronics 225 may determine the baseline resistance values of sensor elements 311. If the baseline resistance values are at or above a certain value, nose chips 310 are reset or discarded and replaced. Method 400 proceeds to step 415.

Step 415: Dispensing Stoppers

In this step, individual stoppers 110 are dispensed into receivers 115 in web 120. For example, software algorithms on conveyor controller 220 (e.g., web controller 240) are used to move rollers 150 and align web 120 with hopper/dispenser 105 such that receiver 115a is directly beneath the hopper/dispenser. Stoppers 110 in hopper/dispenser 105 are dispensed into receiver 115a using software algorithms in hopper/dispenser controller 230 such that a single stopper 110 is dispensed. Web 120 is advanced, for example, in a clockwise direction, and the process is repeated until the appropriate numbers of receivers 115 (e.g., receivers 115b, 115c and 115d) are filled. Method 400 proceeds to step 420.

Step 420: Activating Airflow

In this step, airflow is activated and directed or drawn over stoppers 110 in receiver 115 to extract chemical vapors (e.g., TCA) from stoppers 110. For example, air movers 130 may be activated using software algorithms in air mover controller 250 to provide airflow (e.g., a flow of heated air) over stoppers 110. As air flows past stoppers 110, the chemical vapors from stoppers 110 are mixed with the heated air and are carried toward sensor units 135, where sensor elements 311 on nose chips 310 are exposed to the air/vapor mixture. Method 400 proceeds to step 425.

Step 425: Sensing Analyte

In this step, each sensor unit 135 determines the level of one or more analytes in the air/vapor mixture. The identification of an analyte typically occurs as follows. An electrical signal is provided by power regulator 345 to nose chips 310. A series of electrical traces (not shown) from each of sensor elements 311 of nose chips 310 are connected to provide an electrical path through leads 340 and probe fingers 330 to A/D 360 and microprocessor 350. Microprocessor 350, using instructions stored in memory 355 and in timing and control circuitry 380, converts an electrical signal generated from sensor elements 311 of nose chips 310 into a processed output signal. The instructions stored in memory 355 include, for example, a look-up table that compares incoming signals to stored reference values to provide an analysis. Alternatively, an algorithm or other analytical means for providing a chemical analysis can be provided. In the presence of an analyte, e.g., TCA, a change in electrical resistance is detected and processed by microprocessor 350. The results are output via interface 385 and communication link 210 to computer 205. Method 400 proceeds to step 430.

Step 430: Advancing Web

In this step, web 120 is advanced an appropriate increment to position the receiver, e.g., receiver 115d, in proximity to diverter 145. Method 400 proceeds to step 435.

Step 435: Bad Stopper?

In this decision step, software algorithms in sensor electronics 225 determine whether any of the one or more undesirable analytes being tested, e.g., TCA, is present on stopper 110, as measured by the corresponding nose chip(s). If yes, method 400 proceeds to step 440. If no, method 400 proceeds to step 450.

Step 440: Diverting Stopper

In this step, diverter 145 is activated using software algorithms in diverter controller 260 and a rejected stopper 110 is diverted to reject bin 165. Nose chip 310 corresponding to that rejected stopper 110 may be discarded with the rejected stopper or, alternatively, may be recycled and reset for re-use, depending upon the reusability of the nose chip. Bin full controller 270 may monitor the levels of rejected stoppers 110 in reject bin 165, and a signal is generated when reject bin 165 is full. Method 400 proceeds to step 445.

Step 445: Replacing Nose Chip

In this step, if nose chips 310 are of the non-reusable type, a new nose chip 310 and/or nose chip holder 315 is replaced on web 320. Method 400 may proceed to step 455.

Step 450: Collecting Stopper

In this step, web 120 is advanced an appropriate increment to position the receiver, e.g., receiver 115d, in recess 155 of roller 150a. As receiver 115d is advanced over roller 150a, stopper 110 in recess 155 falls out of receiver 115d into accept bin 160. Bin-full controller 270 may monitor the levels of collected stoppers 110 in accept bin 160 and generate a bin-full signal when the accept bin is full. Method 400 proceeds to step 455.

Step 455: More Stoppers?

In this decision step, it is determined whether additional stoppers 110 are available for screening. For example, the total number of stoppers 110 to be screened are set in step 405 and software algorithms are used to track the number of stoppers 110 dispensed from hopper 105 and screened by sensor units 135 to determine whether a stopper 110 remains to be screened. If yes, method 400 returns to step 410. If no, method 400 ends.

While the present invention has been described in connection with a preferred embodiment, it will be understood that it is not so limited. On the contrary, it is intended to cover all alternatives, modifications and equivalents as may be included within the spirit and scope of the invention as defined above and in the claims appended hereto.

What is claimed is:

1. A method of testing a plurality of cork wine bottle stoppers for the presence of an analyte known to cause cork taint in wine, comprising:
   (a) automatedly moving a first one of the plurality of cork wine bottle stoppers to a first position;
   (b) automatedly moving a first sensor to a second position proximate said first position, said first sensor being operatively configured to detect the presence of the analyte;
   (c) just prior to step (d), placing said first sensor in communication with sensor electronics by contacting a plurality of probes with a plurality of leads that are each in electrical communication with said first sensor;
   (d) determining via said first sensor whether the analyte is present in/on said first one of the plurality of cork wine bottle stoppers;
   (e) automatedly moving said first one of the plurality of cork wine bottle stoppers out of said first position;
   (f) automatedly moving said first sensor out of said second position;
   (g) automatedly moving a second one of the plurality of cork wine bottle stoppers into said first position;
   (h) automatedly moving a second sensor to said second position, said second sensor operatively configured to detect the presence of the analyte; and
   (i) determining via said second sensor whether the analyte is present in/on said second one of the plurality of cork wine bottle stoppers.

2. A method according to claim 1, wherein the analyte comprises 2,4,6-trichloroanisole.

3. A method according to claim 1, wherein each of said first and second sensors is an electronic nose.

4. A method according to claim 3, wherein step (d) includes moving a fluid from the first item to the first sensor so as to transport a portion of any analyte present in said first one of the plurality of cork wine bottle stoppers to said first sensor.

5. A method of testing cork wine bottle stoppers for the presence of an analyte known to cause cork taint in wine, comprising:
   (a) providing at least 100 candidate cork wine bottle stoppers;
   (b) feeding said at least 100 candidate cork wine bottle stoppers into an automated testing system comprising a plurality of electronic noses sensitive to the analyte; and
   (c) causing said automated testing system to test each of said at least 100 candidate cork wine bottle stoppers for the presence of the analyte in rapid succession with others of said at least 100 candidate cork wine bottle stoppers using said plurality of electronic noses and to separate said at least 100 candidate cork wine bottle stoppers into an accepted set and a rejected set, said causing of said automated testing system to test including:

automatedly moving a first candidate cork wine bottle stopper of said at least 100 candidate cork wine bottle stoppers to a first position;

automatedly moving a first electronic nose of said plurality of electronic noses to a second position proximate said first position;

determining via said first electronic nose whether the analyte is present in/on said first candidate cork wine bottle stopper;

just prior to said determining via said first electronic nose whether the analyte is present in/out said first candidate cork wine bottle stopper, placing said first electronic nose in communication with sensor electronics by contacting a plurality of probes with a first plurality of leads that each in electrical communication with said first electronic nose;

automatedly moving said first candidate cork wine bottle stopper out of said first position;

automatedly moving said first electronic nose out of said second position;

automated moving a second candidate cork wine bottle stopper of said at least 100 candidate cork wine bottle stopper into said first position;

automatedly moving a second electronic nose of said plurality of electronic noses to said second position;

determined via said second electronic nose whether the analyte is present in/on said second candidate cork wine bottle stopper; and just prior to said determining via said second electronic nose whether the analyte is present in/on said second candidate cork wine bottle stopper, placing said second electronic nose in communication with sensor electronics by contacting said plurality of probes with a second plurality of leads that are each in electrical communication with said second electronic nose.

6. A method according to claim 5, wherein step (a) includes providing at least 1,000 candidate cork wine bottle stoppers, step (b) includes feeding said at least 1,000 cork wine bottle stoppers into said automated testing system, and step (c) comprises said automated testing system to test each of said at least 1,000 candidate cork wine bottle stoppers for the presence of the analyte in rapid succession with others of said at least 1,000 candidate cork wine bottle stoppers using said plurality of electronic noses.

7. A method according to claim 5, wherein the analyte comprises 2,4,6-trichloroanisole and said plurality of electronic noses are sensitive to 2,4,6-trichloroanisole, step (c) comprising causing said automated testing system to test each of said at least 100 candidate cork wine bottle stoppers for the presence of 2,4,6-trichloroanisole in rapid succession with others of said at least 100 candidate cork wine bottle stoppers using said plurality of electronic noses.

8. A method according to claim 5, wherein the step of determining via said first electronic nose whether the analyte is present in/on said first candidate cork wine bottle stopper includes moving a fluid from said first cork wine bottle stopper to said first electronic nose so as to transport a portion of any analyte present in said first cork wine bottle stopper to said first electronic nose.

9. A cork sorting apparatus, comprising:
(a) a plurality of electronic noses each operatively configured to detect a chemical contaminant known to cause cork taint in wine;
(b) a stopper conveying system operatively configured to hold and move each cork wine bottle stopper of a plurality of cork wine bottle stoppers in rapid succession to a first position;
(c) an electronic nose system operatively configured to move each electronic nose of said plurality of electronic noses, in seriatim, to a second position proximate said first position in concert with said first system;
(d) sensor electronic operatively configured to identify from within said plurality of cork wine bottle stoppers via said plurality of electronic noses:
    (i) accepted cork wine bottle stoppers; and
    (ii) rejected cork wine bottle stoppers; and
(e) a sorting system is configured to separate said rejected cork wine bottle stoppers from said accepted cork wine bottle stoppers;
wherein each of sad plurality of electronic noses is in electrical communication with said sensor electronics substantially only when located in said second position.

10. An apparatus according to claim 9, wherein each of said plurality of electronic noses is operatively configured to sense 2,4,6-trichloroanisole.

11. An apparatus according to claim 9, further comprising a gas moving system for moving a gas so as to move at least a portion of said chemical contaminant, if present, from each one of said plurality of cork wine bottle stoppers when located at said first position to the corresponding respective one of said plurality of sensors located at said second position.

12. An apparatus according to claim 9, wherein each of said plurality of electronic noses is a single-use electronic nose.

13. A cork sorting apparats, comprising:
(a) plurality of electronic noses each operatively configured to detect a chemical contaminant known to cause cork taint in wine;
(b) a stopper conveying system operatively configured to hold and move each cork wine bottle stopper of a plurality of cork wine bottle stoppers in rapid succession to a first position;
(c) an electronic nose system operatively configured to move each electronic nose of said plurality of electronic noses, in seriatim, to a second position proximate said first position in concert with said first system;
(d) sensor electronics operatively configured to identify from within said plurality of cork wine bottle stoppers via said plurality of electronic noses;
    (i) accepted cork wine bottle stoppers; and
    (ii) rejected cork wine bottle stoppers; and
(e) a sorting system is configured to separate said rejected cork wine bottle stopper from said accepted cork wine bottle stoppers;
wherein said sensor electronics are operatively configured to, in seriatim, make each of said plurality of electronic noses operational for sensing the presence of said chemical contaminant and
wherein said sensor electronics include a plurality of probes and each one of said plurality of sensors including plurality of leads for contracting said plurality of probes, the apparatus further comprising a fourth system that moves at least one of said plurality of probes and one of said plurality of probes so that said plurality of probes and said plurality of leads contact one another.

* * * * *

UNITED STATES PATENT AND TRADEMARK OFFICE
CERTIFICATE OF CORRECTION

| | | |
|---|---|---|
| PATENT NO. | : 7,290,438 B2 | Page 1 of 1 |
| APPLICATION NO. | : 11/372848 | |
| DATED | : November 6, 2007 | |
| INVENTOR(S) | : Michael S. Head et al. | |

It is certified that error appears in the above-identified patent and that said Letters Patent is hereby corrected as shown below:

In the Claims

Column 13, claim 5(c), line 11. Specifically, delete the word(s) "in/out" and replace to read as "in/on"

Column 13, claim 5(c), line 15. Specifically, insert the word --are-- before each, to read as "leads that are each in"

Column 14, claim 9(e), line 17. Specifically, delete the word "sad" and replace to read as "said"

Column 14, claim 13, line 33. Specifically, delete the word "apparats" and replace to read as "apparatus"

Column 14, claim 13(a), line 34. Specifically, insert an --a-- before plurality, to read as "a plurality of"

Signed and Sealed this
Third Day of June, 2014

Michelle K. Lee
*Deputy Director of the United States Patent and Trademark Office*